(12) United States Patent
Andersson et al.

(10) Patent No.: US 7,175,435 B2
(45) Date of Patent: Feb. 13, 2007

(54) METHOD, ARRANGEMENT AND PROGRAM FOR A PROSTHETIC INSTALLATION

(75) Inventors: Matts Andersson, Lerum (SE); Izidor Brajnovic, Göteborg (SE)

(73) Assignee: Nobel Biocare AB, Göteborg (SE)

( * ) Notice: Subject to any disclaimer, the term of this patent is extended or adjusted under 35 U.S.C. 154(b) by 567 days.

(21) Appl. No.: 10/451,535

(22) PCT Filed: Dec. 27, 2001

(86) PCT No.: PCT/SE01/02898

§ 371 (c)(1),
(2), (4) Date: Jun. 24, 2003

(87) PCT Pub. No.: WO02/053056

PCT Pub. Date: Jul. 11, 2002

(65) Prior Publication Data

US 2004/0078212 A1  Apr. 22, 2004

(30) Foreign Application Priority Data

Dec. 29, 2000  (SE) .................................. 0004884

(51) Int. Cl.
*A61C 5/00* (2006.01)
*A61C 9/00* (2006.01)
(52) U.S. Cl. ........................ 433/215; 433/213; 433/214
(58) Field of Classification Search ........ 433/213–215, 433/54

See application file for complete search history.

(56) References Cited

U.S. PATENT DOCUMENTS 4,906,420 A  3/1990  Brajnovic et al.

5,851,115 A * 12/1998 Carlsson et al. ............ 433/215

FOREIGN PATENT DOCUMENTS

SE  457 691 A  1/1989
WO  WO 98/44865 A1  10/1998

* cited by examiner

*Primary Examiner*—Cris L. Rodriguez
*Assistant Examiner*—Candice C. Stokes
(74) *Attorney, Agent, or Firm*—Venable LLP; Eric J. Franklin

(57) ABSTRACT

In a method and arrangement for allocating prosthetic installation work between at least three parties (A, B, C) a dental situation and fixture application are simulated on a computer screen by the first party. The second party produces first components in connection with the prosthetic installation with the aid of a recording and said simulation. Second components are supplied by the third party (C) and the prosthetic installation is assembled and fitted by the first party by means of said first and second components. The recording includes first and second readings of a loose prosthesis and a portion supporting the prosthetic insallation. The simulation includes collation of representations of the readings on a computer screen. Simulated fixture applications are constructed and a model is produced by one of said parties, or a fourth party. An assembly template guides hole-forming members in an actual substrate in directions which correspond to the directions of the fixtures. A dental bridge is provided with attachment holes which connect to the holes formed in the substrate. Fixtures are applied in said formed holes by the first party and the dental bridge is secured in or on said fixtures. The invention also relates to a computer program in connection with the above.

19 Claims, 7 Drawing Sheets

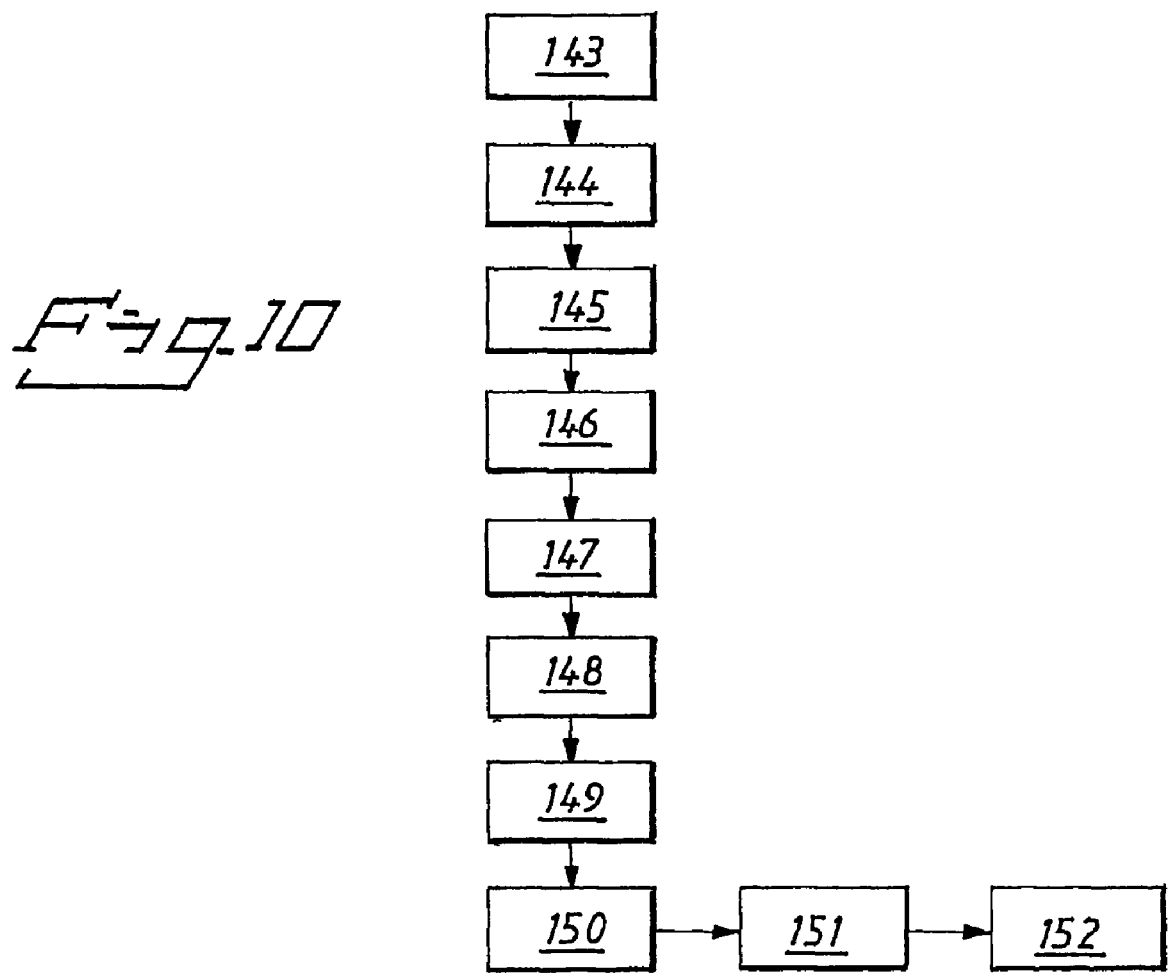

METHOD, ARRANGEMENT AND PROGRAM FOR A PROSTHETIC INSTALLATION

Figure 1:
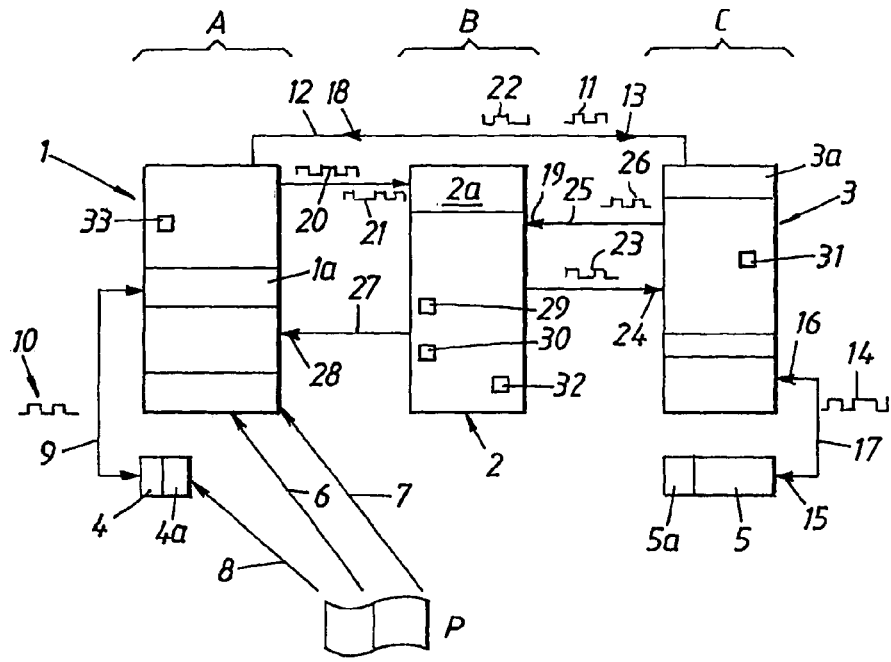

The present invention relates to a method for allocating prosthetic installation work between at least three parties, where a dental situation and fixture applications therein are simulated on a computer screen (in computer equipment) by the first party, first components in connection with the prosthetic installation are produced by the second party with the aid of a recording and said simulation, second components are supplied by the third party, and the prosthetic installation is assembled and fitted by the first party by means of said first and second components. The invention also relates to an arrangement connected with this method.

The invention also concerns a method for replacing, in a short application time, a loose prosthesis with a fixed installation in a completely or partially edentulous patient. A short application time is understood, for example, to be a time of 1 to 4 hours, for example ca. 1½ to 2 hours. The arrangement is intended for applying fixed installations, for example in the form of dental bridges, in patients who are completely or partially edentulous, at least in one jaw bone, preferably the upper jaw bone. The arrangement can comprise first units (or items of equipment) with the task of determining measures in the various patient cases, dealing with the production of computerized representations with fitted fixture applications in the various cases, producing working models of the desired installations and opposite jaw bone, ordering the production of dental bridges and fixtures and securing members for securing the dental bridges, and effecting the application of the fixtures and the securing of the installations or dental bridges in the patients' jaw bones. Said first units or items of equipment are related to dentists, dental specialists, prosthetists, surgeons, clinics or hospitals for X-ray tomography, etc. Second units or items of equipment which represent or are located at dental technicians or the like use information relating to the computerized representations and the working models to produce templates for forming fixture holes on the patients and the patients' dental bridges. A third unit or item of equipment which represents a supplier of basic elements and/or structural parts (cf. PROCERA) receives from the first units or items of equipment, via ordering and distribution channels, the order for fixtures and accessories which are necessary for executing the various orders for different patients. The ordering and distribution channels can comprise or consist of telecommunication and/or computer links, it being possible for the Internet to form or be part of one or more links. The arrangement can thus permit, within said short time, the application of a prosthetic installation by means of structural parts, dental crowns, dental bridges, etc., received from a second party who can include said dental technicians, and components, for example implants, spacers, securing screws, etc., received from a third party, who can be a producer of basic elements and structural parts. The structural parts can be extracted with production parts which can consist of models, templates, impressions, readings, tools, etc., and equipment or items of equipment for complete or partial production of the production parts, which equipment or items of equipment are owned by or available to at least the third party, which signifies that in an alternative embodiment the third party is able in turn to arrange the production to be done by a further party specialized in the particular production part or production parts. The arrangement can thus permit, with considerable precision requirements, the securing of a particular dental installation in a jaw bone or other bone of a patient by means of fixtures and securing members. The arrangement can in this case comprise or operate with first equipment for imaging the jaw bone and possible prosthesis, second equipment for reproducing representations of the jaw bone and possible prosthesis in computer equipment, said computer equipment being intended to permit virtual or planned fixture application in the representation. The arrangement also comprises or operates with third equipment for producing an installation part based on the representation, and fourth equipment for producing working models, by means of which attachments can be made on the installation part and the latter can be finished. The invention also relates to an arrangement which permits a responding party to supply to an inquiring party or parties information which may concern the prosthetic installation and the work associated with the latter. A computer is in this case designed to simulate a dental situation and fixture applications therein. One or more production units are arranged to produce components intended for the prosthetic installation and for fitting the latter, and equipment located at the respective inquiring party is designed to permit or prepare the prosthetic installation. In addition, the arrangement is intended to permit the supply of components or products for prosthetic installations and the design of these from the producing party to the party ordering the components. The supply is in this case based on the handling of orders, finances, invoices, the components or the products and the ordering parties, i.e. the customers. The invention also proposes a program stored on a computer medium for generating a protocol with the aid of one or more computers for production, fitting and/or monitoring of the production and fitting of dental prosthetic installations. One party or unit in this case supplies components or products for the prosthetic installations and the designs of these. The parties or units ordering said components or products prepare and install the prosthetic installations.

In connection with installations of this type, it is already known to use X-ray tomography and other imaging principles in order to exactly determine the respective dental situation of the patient. It is known to use computer equipment located with a dentist, prosthetist, dental experts, etc. and to input into the computer equipment representations from the radiography and impression results and to virtually adapt and apply fixtures in connection with said representations. Reading apparatus, for example for reading off a loose prosthesis or the like, are known per se. The apparatus can work according to different principles, for example laser scanning principles, photo principles, etc. It is also already known to use production functions for a dental or other body-related model with the aid of stereolithography.

Reference is made in purely general terms to "Computer Technology", published by Jos Vander Sloten ???? 2000. Reference is made in particular to the section "An image-guided planning system for endosseous oral implants" by Kris Verstreken et al., pages 192–240.

Reference is also made in purely general terms to Handboek Orale Implantaten 1999, Bohn, Stafleu.

Reference is also made to various lecture programmes and courses arranged by ??? prior to May 2000.

Reference is also made to the PROCERA SE production system which concerns computerized and automated production of basic elements, models, tooth replacements (e.g. sleeves, dental crowns, etc.). Reference is made in this connection to the patents and patent applications WO 98/44865 and ???? owned by Nobel Biocare AB, Sweden. Reference is also made to Swedish Patent SE 457,691 with the same owner and relating to the production of dental products by means of carbon fiber-reinforced plastic. Reference is also made to the Swedish applications filed by the same Applicant as the present application, namely "Device for determining position", "Method and device for a dental unit or unit intended for the human body", and "Device for forming holes and inserting sleeves in a unit included in a dental attachment part".

Reference is also made to the range of products commercially available from Nobel Biocare AB, Sweden, namely sleeves, dental bridges, fixtures, securing members, tools, apparatus, instruments, etc.

It is already known to design a fixed installation for a patient who is completely or partially edentulous and wishes to have an installation fitted, for example instead of an already existing prosthesis. The installation work in question has been extremely time-consuming and has involved a number of trials on the patient covering a long period of time which has extended over weeks and months. The patient has found such treatments inconvenient and for this reason has been unwilling to accept or has completely refused to undergo the treatment in question. There is now a general need to reduce the actual treatment time for the patient. The present invention deals with this problem and proposes that the actual insertion or implantation of the fixed installation must be able to be carried out in an extremely short time, for example in one day or part of a day.

The present invention is based on the recognition that the precise fitting work which was previously carried out on the patient can be undertaken outside the patient by means of the exactness or precision being built into, on the one hand, the equipment used by the parties involved (the units, equipment) for the different parts of the installation, and on the other hand into the production of models with the aid of apparatus/tools, and also into the basic elements for the structural parts, and the structural parts themselves. The invention solves this problem too.

In connection with the production of the installations and the fitting of the installations, there are considerable cost restraints on the parties who are concerned with the production and the installation of the tooth replacements in question (e.g. dental crowns). A problem which the invention solves in this connection is that of providing a way of allocating the finances provided for in each individual case between the different parties. It is important that the allocation of work and the routines surrounding the handling between the parties are so efficient that the economic target can be fulfilled despite the considerable precision requirements imposed on the installations in question. The invention also solves this problem and proposes production principles, work allocation principles and advantageous debiting principles for said installations. Among other things, the third party (who in some of the subsequent arrangements of the parties has also been referred to as the second party in the chain, and this for technical reasons) must be able to ensure efficient and accurate distribution and debiting of the basic elements, parts and services involved. The second party (who for technical reasons can also be referred to as the third party in certain cooperation formats) must be able to perform his part of the work and satisfy the precision requirements which have been set. The first party must, as previously, be responsible for diagnostics and produce images and models of the patient and carry out the final installation work in a very short time. The debiting and mutual allocation of the resources provided must in this case be able to be done in accordance with what is proposed by the invention.

It is important that apparatus and methods and elements which are known per se and well proven can be used for the production of the installations and fitting of the installations in question. The invention also solves this problem and is based on known techniques and known methods being able to be used as far as possible.

It is known that a large number of dental crowns and dental bridges, for example ceramic crowns or dental bridges (AC crowns; AllcerAM) have been produced and fitted during the last ten years. These have been produced by, among others, Nobel Biocare, Gothenburg, Sweden. The system known as the PROCERA CAD/CAN system has been used, in which a detailed recording of, inter alia, preparation surfaces has been stored in digital form as complete data files combined with identification of tooth type and orders via the computer network. These data files permit visualization of each preparation on a computer screen, and the two-dimensional profiles thus obtained have been used in earlier studies in order to obtain an overview of the various structures on the preparations. In this respect, it has been found that there is a great variation between different groups of dentists. It is therefore possible to further refine the recommendations for the installation work and the structures on the installations. The invention also solves this problem.

The features which can principally be regarded as characterizing a method according to the invention are that the recording includes a first reading of an impression or prosthesis (tooth structure) and a second reading of a portion (all or part of a jaw) supporting the prosthetic installation, that the simulation includes collation of images or representations on the computer screen, which images or representations result from the first and second readings and on the basis of which the simulated fixture applications are constructed, and that the simulated fixture applications include chosen positionings in relation to said supporting portion. The method is further characterized by the fact that a model, for example made of plastic, is produced, preferably by a stereolithography method, by one of said parties, or a fourth party, and that the first components include an assembly template which can be applied to said substrate and is produced by means of the model and is intended for hole-forming members which are guided by the assembly template in the substrate in directions which correspond to the directions of the chosen positionings. Finally, the method can be considered as being characterized by the fact that the first components include a unit forming part of the installation, for example a dental crown, which is provided with attachment holes which connect to the holes formed in the substrate, that the second components include the fixtures which are applied in said formed holes by the first party, and that the second components also include securing members, for example securing screws, for securing the unit in said applied fixtures.

Further developments of the method are set out in the attached dependent claims concerning said method.

The features which characterize an arrangement according to the invention are, inter alia, that the recording includes a first reading of an impression or prosthesis (tooth structure) and a second reading of a portion (all or part of a jaw) supporting the prosthetic installation, that the computer (i.e. its program) is intended, in connection with the simulation, to permit collation of images or representations on the computer screen, which images or representations result from the first and second readings, and to indicate on these the simulated fixture applications which include chosen positionings in relation to said supporting portion, and that second equipment, preferably stereolithography equipment, which is located with one of the parties, or with a fourth party, is intended for production of a model, for example of plastic. Further characteristics are that the first production unit is provided for production of an assembly template which has been constructed by means of the model and which has guide elements for hole-forming members which can be guided by the assembly template in order to assume directions which correspond to the directions of the chosen positionings, and that the first production unit is also provided for production of a structural unit or structural part, for example a dental crown, which forms part of the installation and which is provided with attachment holes which connect to the holes formed in the substrate. Further characteristics are that the second production or supply unit produces or supplies the fixtures intended for said formed holes, and also securing members (for example, screws) for securing the structural unit in the fixtures which are applied in the substrate. Further developments of the novel arrangement are set out in the dependent claims concerning said arrangement.

The invention relates to different method steps, where a first step includes control, for example primary radiography, of the jaw-bone status by the first party who in this case can be a dentist, dental specialist, prosthetist, etc. If the status is acceptable, X-ray tomography is performed by a surgeon, hospital, clinic, who or which have access to the radiography equipment in question. A simulated first representation of the X-ray tomography is input into the computer equipment, preferably by the first party. A simulated second representation of a scanning or reading of a loose prosthesis is additionally input into said computer equipment, which scanning or reading can be carried out by the first party or second party. The first and second representations are coordinated in the computer equipment, in connection with which virtual fixtures are placed in position by the first party, who in this case can be a dentist, prosthetist, dental expert, etc. The result thus obtained is transferred, preferably via the telecommunications and/or computer network, which can include the Internet, to a second party who in this case is a producer of dental basic elements and structural parts (cf. PROCERA) in the form of computer information or digital information which can be related to the first and second representations, said coordination and said virtual fixtures. Thereafter, production of the actual model is carried out on the basis of the information thus transferred and thus received, and preferably with the aid of stereolithography, which model can be a plastic model of the first and second representations, this being done by the second party who owns or has access to stereolithography equipment. Elements are introduced into the actual model, for example tubular elements which extend and are placed in positions and directions corresponding to the positions and directions for the virtual fixtures. The actual model is thereafter transferred to a third party who in this case is a dental technician or the dental laboratory. A loose prosthesis model, preferably made of wax, is also transferred to the third party, preferably from the first party, together with a jaw model of the opposite jaw, which last-mentioned model can be made of plaster. In addition, a bite register index is transferred to the third party, i.e. the dental technician. The third party (the dental technician) uses an articulator in order to produce the patient's bite configuration by means of said loose prosthesis and jaw models and bite register index, taking into consideration the soft-tissue space between jaw bone and teeth. The third part (the dental technician) uses the jaw model to produce an assembly template with a defined position of application to or in relation to the jaw model and thus in relation to the patient's jaw and with identified directions and positions for fixture dummies and thereby for the planned recesses in the patient's jaw bone. Production by the third party (dental technician) of a tooth replacement, for example the dental bridge, by means of the jaw model, and finally the assembly template and the produced tooth replacement or dental bridge are transferred to the first party (dentist, prosthetist, surgeon, etc.) who, by means of the assembly template, forms holes for the planned fixture insertions and, after insertion of the fixtures in the holes, anchors the dental bridge to the fixtures thus inserted.

Another characteristic is that the supplier of basic elements and structural parts (called the third unit in another related case) supplies basic sets of elements, which can consist of fixtures, securing screws, tools, etc., to the first units which are dentists, dental specialists, prosthetists, etc., as a function of first orders. The basic sets can in this case cover the different variations which can arise in the particular dental situations which can consist of applying dental bridges to completely or partially edentulous patients. On the basis of second orders, the last-mentioned supplier of basic elements and structural parts (PROCERA) supplies accessory elements belonging to the basic sets, which accessory elements make it possible to deal with differences in the jaw-bone status and jaw-bone sizes of patients. In other words, as is known per se, the patients have jaw bones of different sizes and structures and for this reason said accessory elements to the basic set are required in order to permit effective treatment by the dentist, prosthetist or the like.

The producer of basic elements and structural parts (PROCERA) or the third party owns, or has available to it, equipment designed to operate with an ordering function in which the equipment receives, via a telecommunications and/or computer link, for example including the Internet in accordance with the above, information relating to a dental situation with jaw-bone structure simulated on computer by the first party, a model of the installation applied to this, and fixtures (implants) applied in the jaw-bone structure and belonging to the abovementioned components, and in addition the equipment belonging to the producer of basic elements and structural parts is designed to operate with stereolithographic production of an actual model, for example made of plastic, of said simulated jaw-bone structure and simulated model, which actual model is included in said production parts.

The components and optional production parts held by the third party (producer of basic elements and structural parts) can in this case be arranged in platforms which are adapted in dimensions to different sizes in different dental situations (i.e. greater or lesser widths, heights, etc., of the jaw bone and installations in question). Thus, treatment arrays for different situations can be offered. The basic arrays can be presented in different platform situations, where a first platform relates to the dimensions "wide", "regular" and "narrow", which thus relate to the jaw-bone structures.

The invention can also relate to an arrangement with different items of equipment, in which first equipment is designed for imaging the jaw bone and any prosthesis, second equipment for reproducing a representation of the jaw bone and the possible prosthesis in the computer equipment, said computer equipment being designed to permit virtual fixture application in the representation, third equipment for producing an installation part based on the representation, and fourth equipment for producing working models by means of which attachments can be effected on the installation part and the latter can be finished. The arrangement in question, preferably the fourth equipment, is designed to produce hole-forming templates which can be applied with precision to the jaw bone, and the items of equipment operate with an accuracy which satisfies said considerable precision requirements and eliminates the need for carrying out sample trials on the patient between the stages of imaging and hole formation, all this with the aim of achieving a short time for securing the installation, which short time can be, for example, 1 to 3 hours, during which holes are formed and fixtures applied and the installation is secured in the implanted fixtures.

The invention is also characterized in that between the abovementioned ordering and production functions (equipment) there is a storage arrangement for likewise abovementioned handling. The storage arrangement will be of modular design with a substantially identical or corresponding structure for each module. The modules can be expanded or reduced on the basis of the number of new customers or departing customers. Alternatively, the customer clientele may change character and/or be redistributed.

The invention also relates to the fact that a data-processing arrangement can contain or receive data or information relating to selected parameters of installations previously produced in the practice. The data-processing arrangement can be designed to receive and compare one or preferably several parameters of the current prosthetic installation with a corresponding parameter or corresponding parameters of said selected parameters. Said information can represent the result of the particular comparison and can, for example, relate to one or more properties of the prosthetic installation, for example strength, esthetic appearance and/or color. In addition, the information can consist of or comprise details and/or data to the effect that the prosthetic installation conceived of by the inquiring party and/or the associated work on this installation is within a risk zone and unacceptable.

The invention also refers to a program stored on a computer medium for generating a protocol with the aid of one or more computers in the production, fitting and/or monitoring of the production and fitting of dental prosthetic installations, where a party or unit supplies components or products for the prosthetic installations and the design of these, and where ordering parties or units who ordered said components or products prepare and insert the prosthetic installations. The features which can principally be regarded as characterizing the program are the stages comprising: definition of patient and his/her tooth and/or jaw-bone status, definition of work procedure for the patient based on production and comparison with stored data relating to similar or corresponding prosthetic installations; definition of the advantages with the current prosthetic installation; definition of models, for example drill model; definition of X-ray tomography; definition of two-dimensional or three-dimensional CADD equipment; definition of model production by means of stereolithography; definition of model production by dental technicians; and definition of preparations by surgeon. The definitions in question take place in parallel with production of definitions of variables, documents, forms, folders and/or envelopes.

By means of what has been proposed above, the work time on patients is surprisingly shortened. After said short time, the patient can already leave the dentist, prosthetist, surgeon, etc., with a fixed installation applied in his jaw. The fixed installation can incorporate effectively without too much inconvenience to the patient, who thereby avoids a protracted process involving insertion of fixtures and tests being done on these, which tests have hitherto comprised a number of trials. The precision requirements can be built-in with the second and third parties, i.e. the dental technician or the dental laboratory and the supplier of the basic elements and structural sets (cf. PROCERA). The already known range of basic elements and structural parts can also continue to be used, and the invention affords the dental technician or the dental laboratory a method and equipment which simplify and shorten their work, while satisfying the professional requirements. Existing debiting and distribution channels can be used by the third party (PROCERA) which in this respect has available to it or owns an advanced debiting and distribution system. Some parts of the method and the equipment operate with dental technology, and the information for X-ray, scanning, imaging etc. can be transmitted digitally in a manner known per se. The various digital representations of advanced X-ray imaging, advanced models and structural parts (obtained by stereolithography, for example) can be easily transferred via existing links in the telecommunications and/or computer network. Computer programs for producing the models in question with very great precision are available on the market and can be used in this context. Said exact models can be used as structural models by the dental technician or the dental laboratory, which receives guarantees of the required precision in connection with dental installations. The invention also affords refined treatment methods in connection with the production of models, templates, etc., and also structural parts and installations which are to be used by the dental technician, prosthetist, dental expert, surgeon, etc. In accordance with the invention, algorithms can be developed for calculation and computer. programming in order to collate and handle different data parameters for example characterized by form and installations of a large number of preparations. Thus, it is possible to calculate a certain number of characteristic parameters concerning the shape of the preparation, compare these with visual characteristics for the preparations, establish the most frequent differences from an ideal, and study possible geographically related variations. It is possible to propose corrections in the event of critical differences from ideal preparations and also to indicate failures which occur upon insertion of the installation or some time after the use of the installation by the patient. A computer program can calculate variations of critical parameters in each installation, which can mean that the useful life of future installations may be extended.

Figure 2:
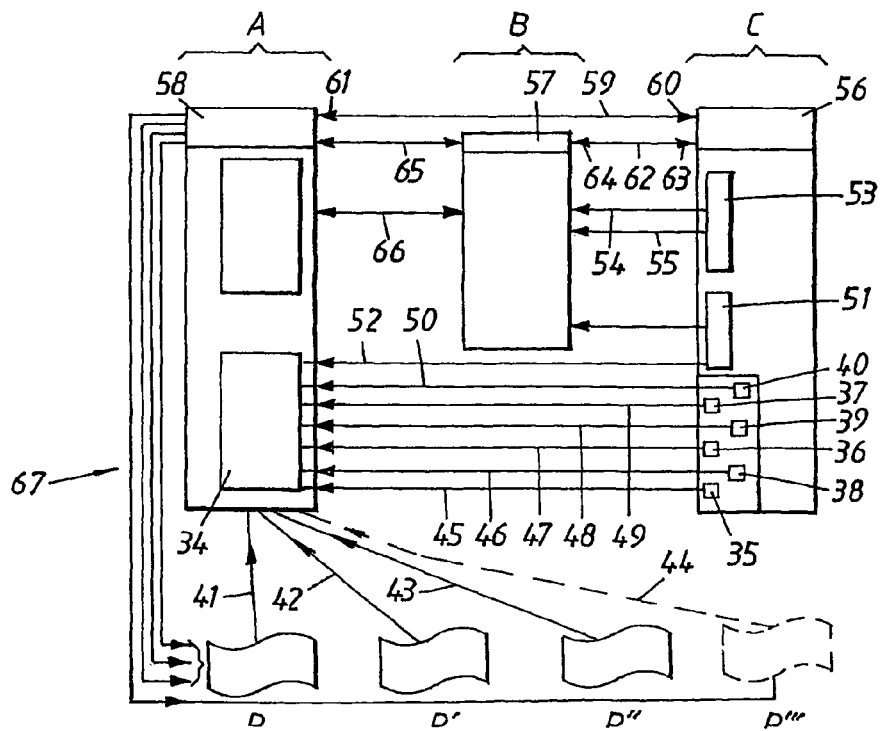
Figure 3:
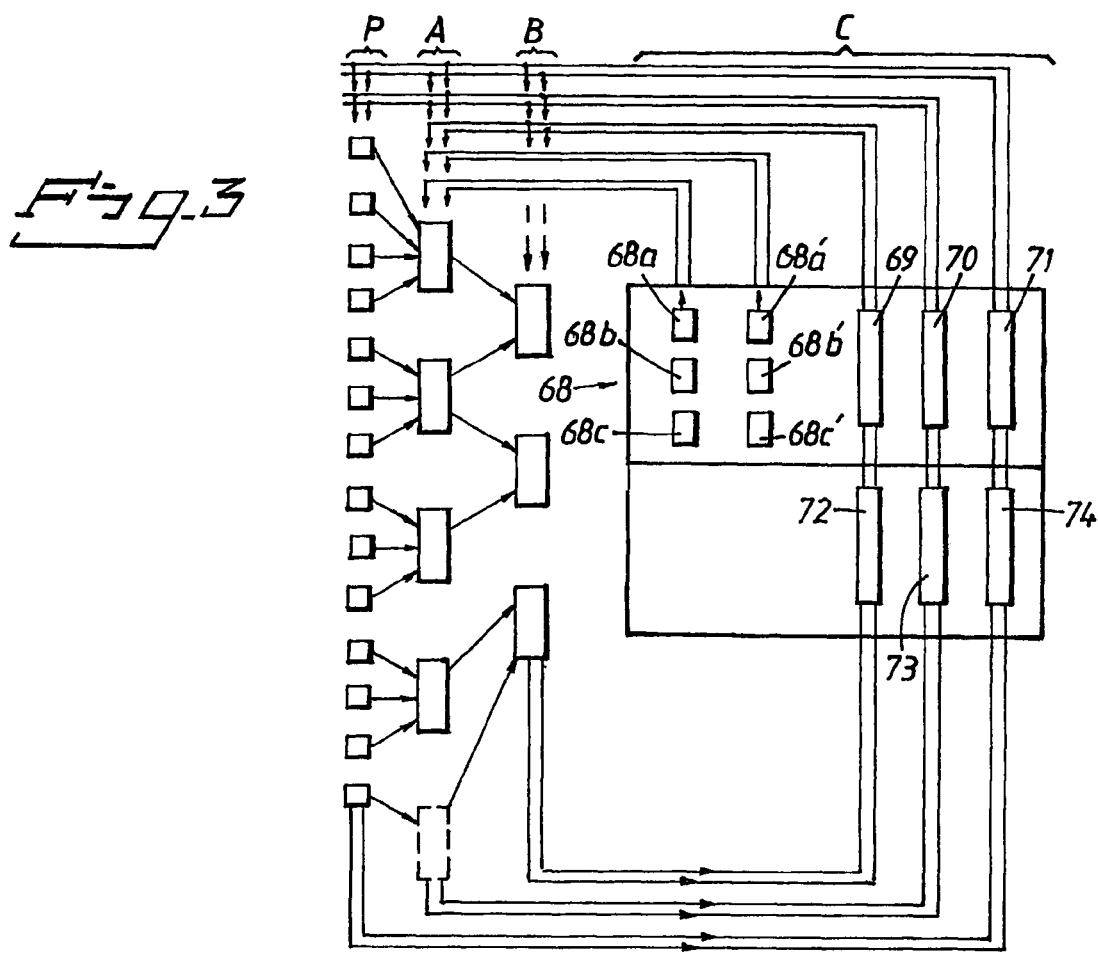
Figure 4:
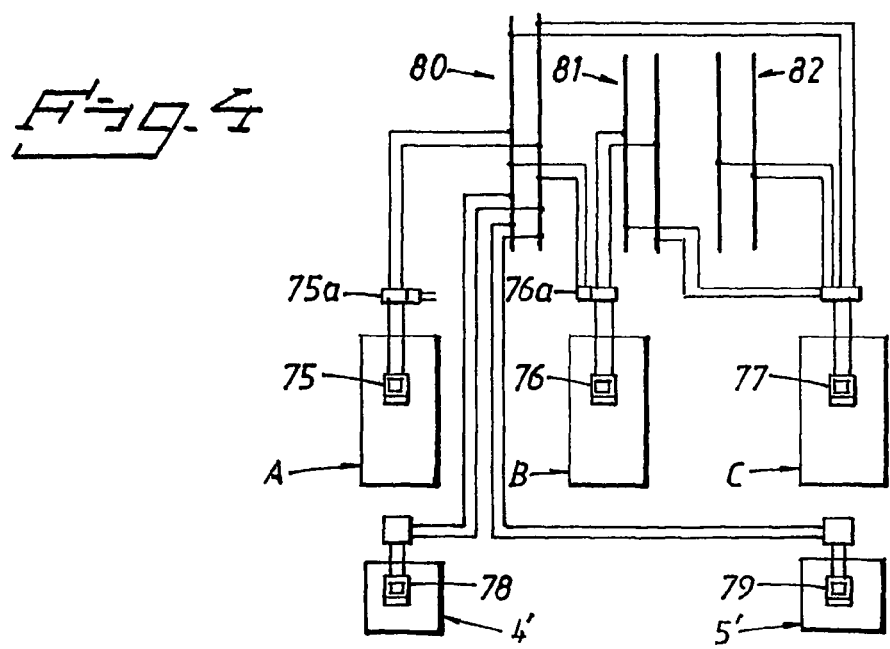
Figure 5:
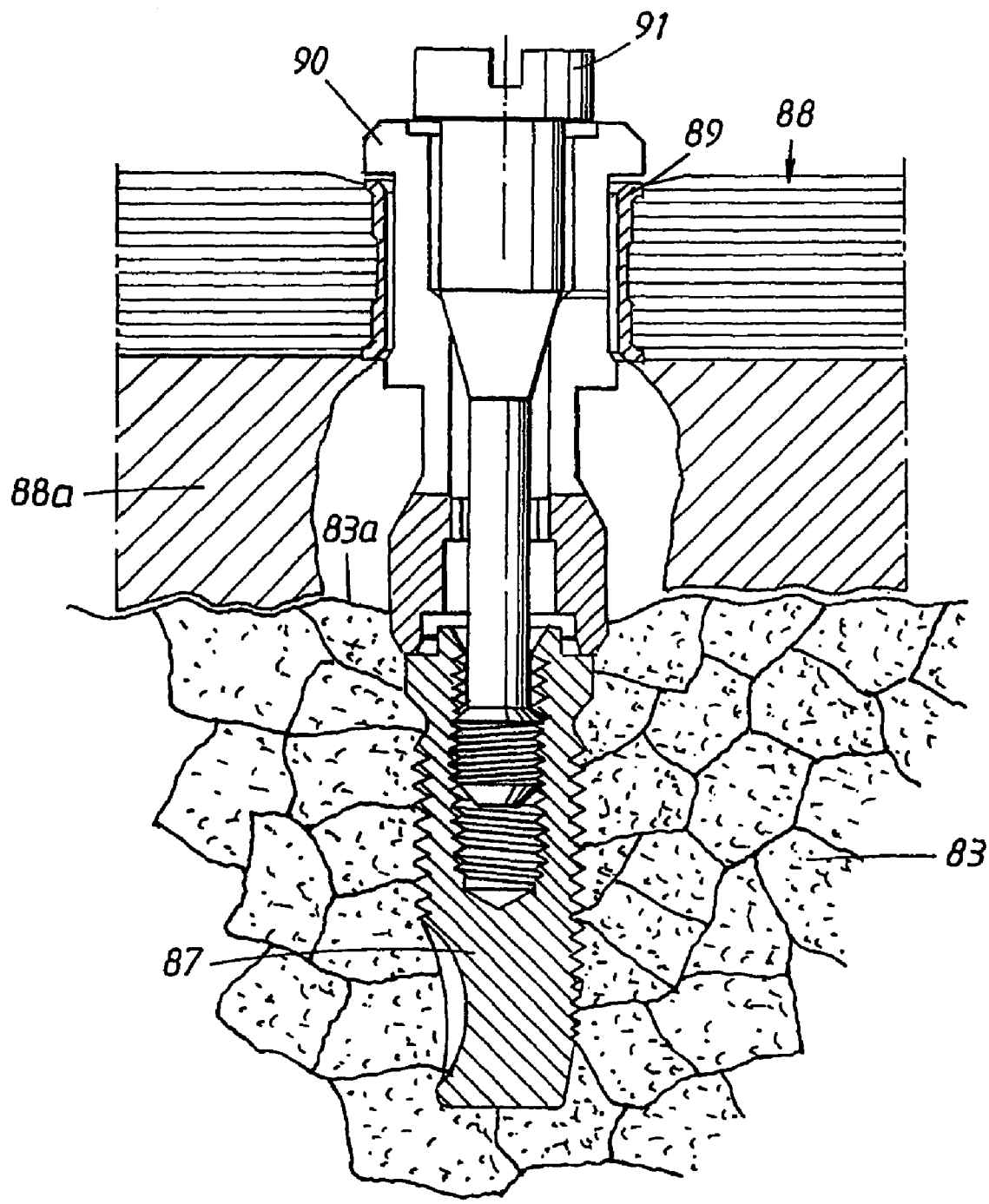
Figure 6:
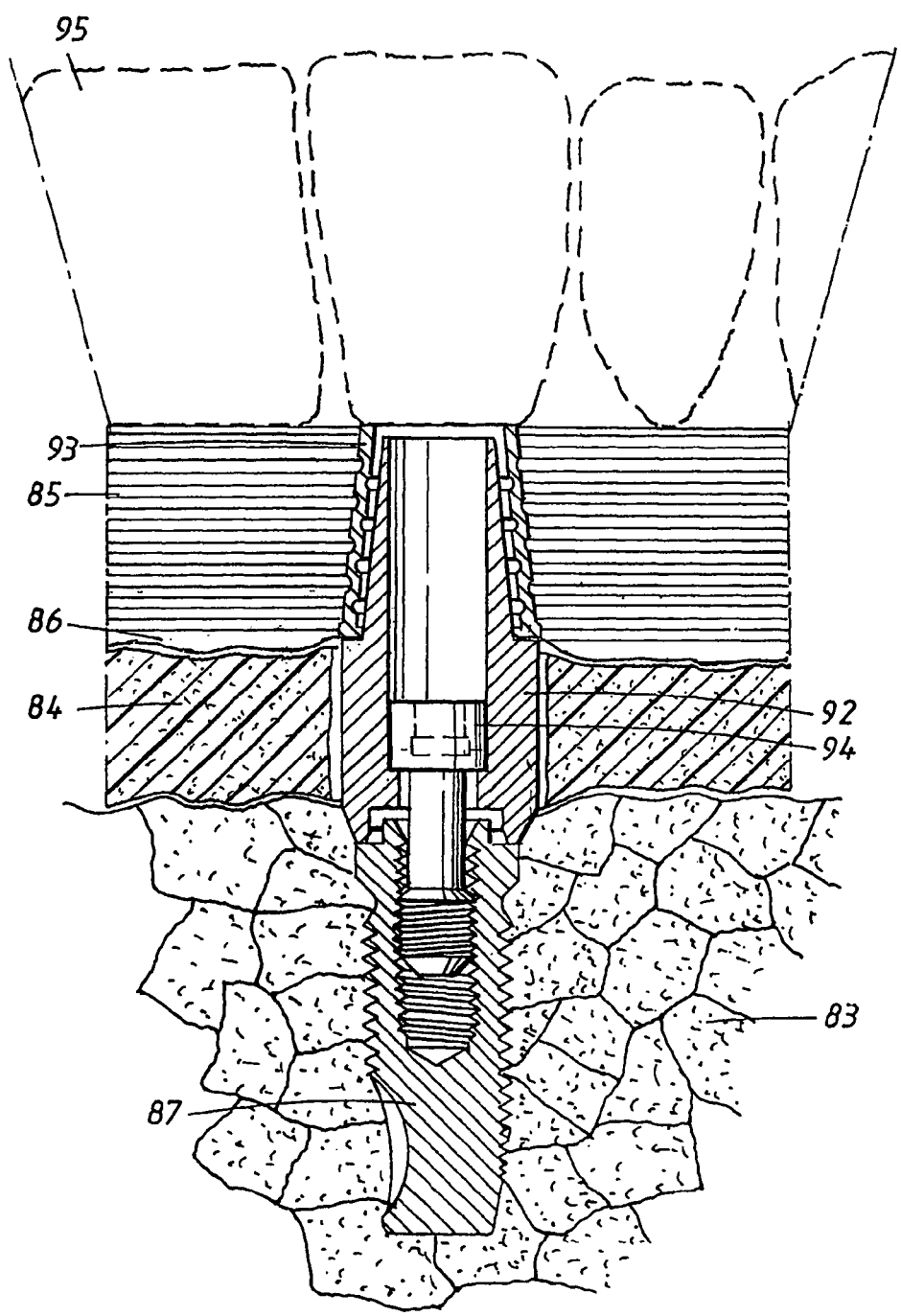
Figure 7:
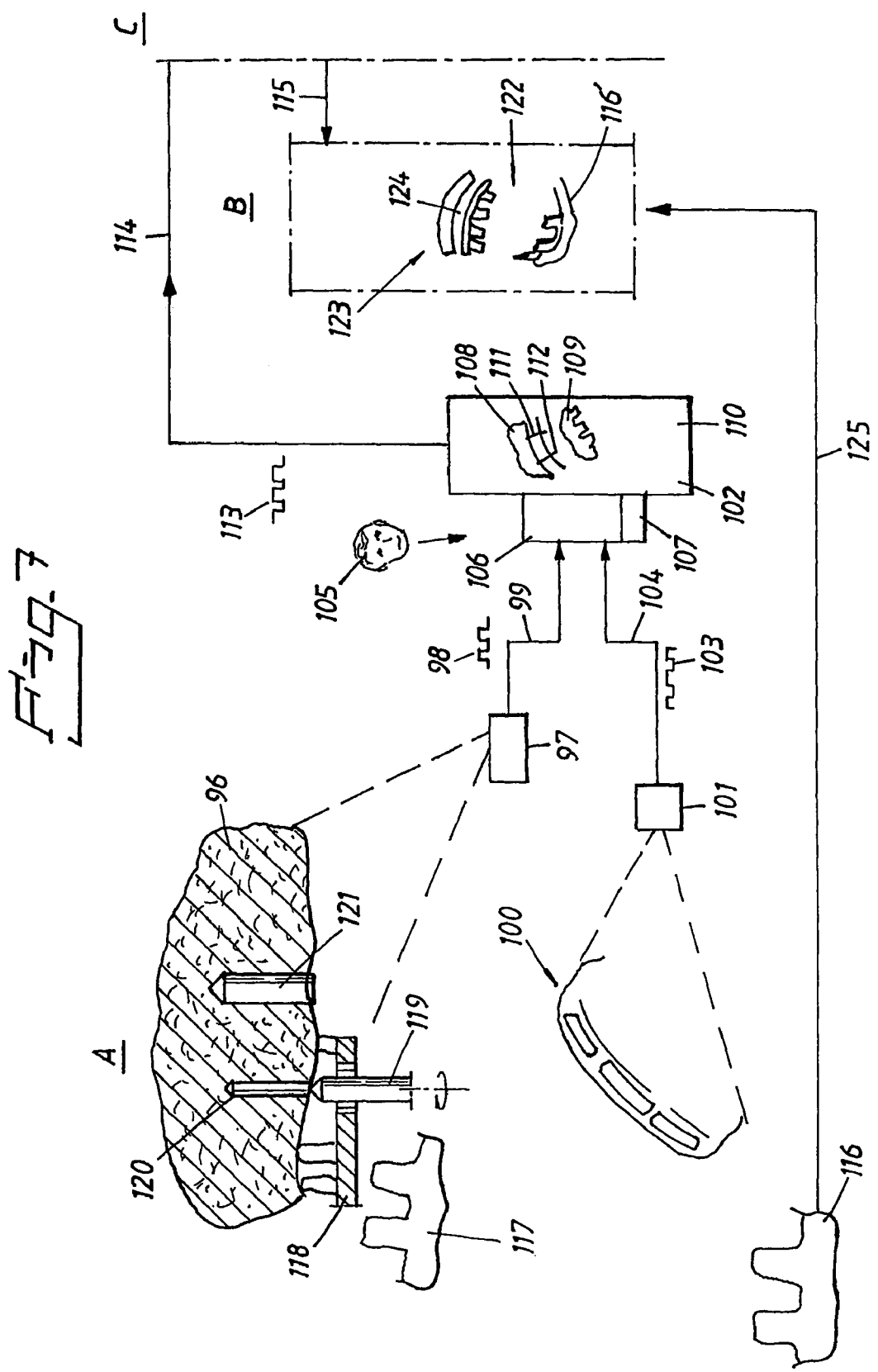
Figure 8:
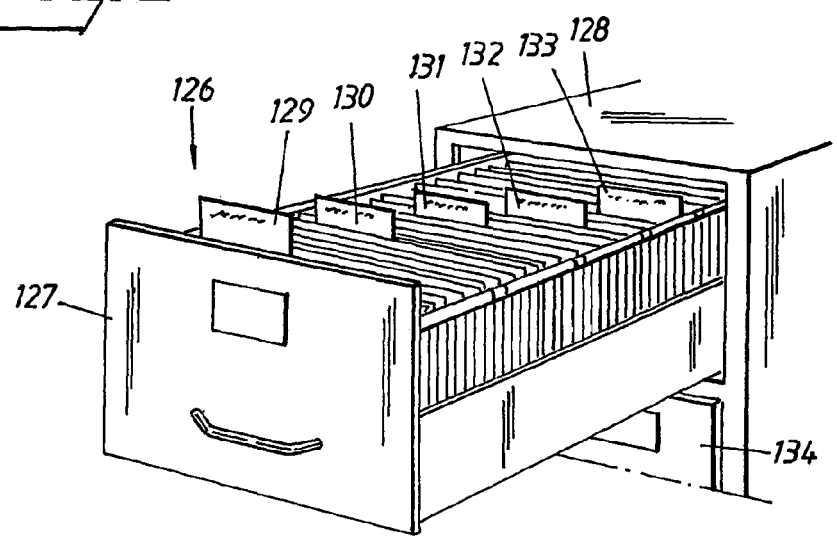
Figure 9:
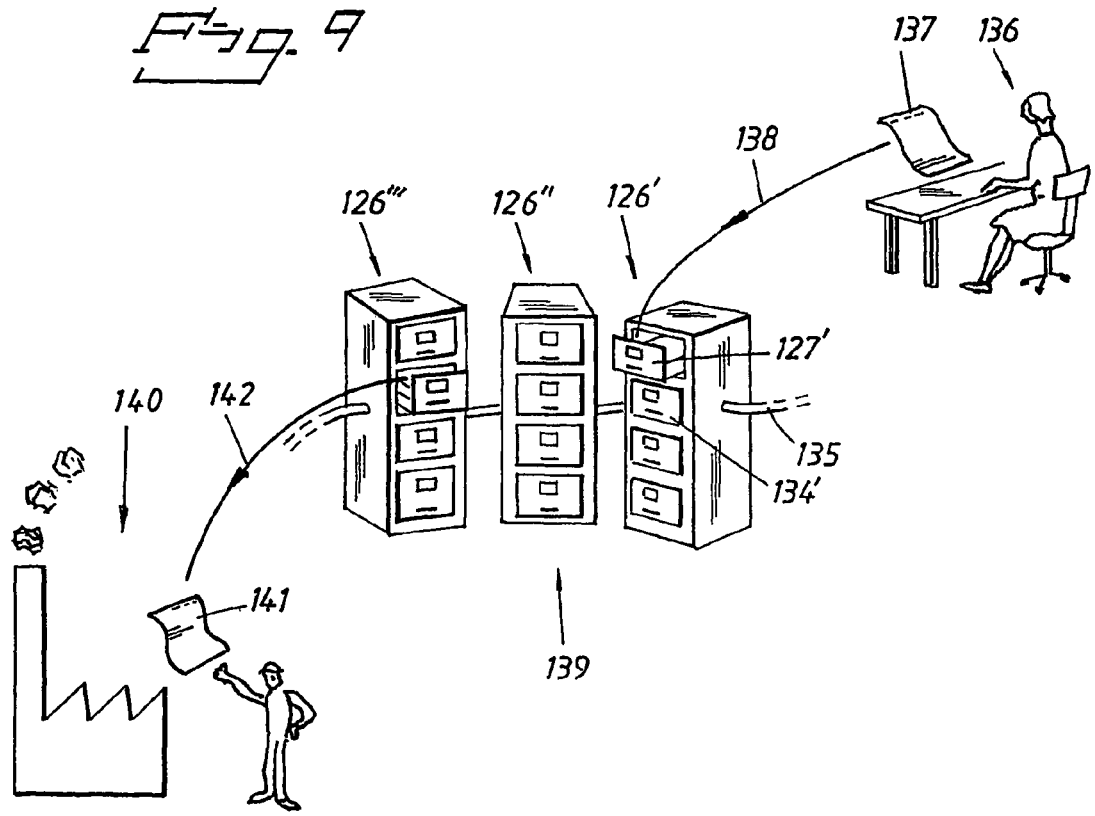

A presently proposed embodiment of an arrangement and method will be described below with reference to the attached drawings, in which:

FIG. 1 is a basic circuit and block diagram showing the patient and three parties involved in supplying a fixed installation for the patient's jaw bone, and the flow of components, structural parts and basic elements between the parties, and also the debiting functions connected with the above, FIG. 2 is a basic circuit and block diagram showing the distribution and debiting paths for the parties involved, FIG. 3 is a basic circuit and block diagram showing how a large number of patients can turn to a large number of first parties who in turn are served by a smaller number of dental technicians or dental laboratories who in turn are served by a third party (PROCERA), FIG. 4 is a basic circuit and block diagram showing how the parties A, B and C are interconnected with their computer equipment via different types of links, FIG. 5 is a vertical section and partial cutaway view showing the production of a hole-forming template (assembly template) using a model which images the jaw bone, and a fixture dummy and expansion spacer and expansion screw applied in the model, FIG. 6 is a vertical view and partial cutaway view showing parts of the dental installation applied on or in a jaw bone, FIG. 7 is a basic circuit diagram showing the cooperation between the parties or the units A, B and C, FIG. 8 is a perspective and symbolic view showing the commercial handling of installations and customers associated with the installations, FIG. 9 is a perspective view showing a module system for handling according to FIG. 8, and FIG. 10 shows a flow chart for a dental installation on a patient.

In FIG. 1, a patient is symbolized by P and three parties by A, B and C, a first party being a dentist, prosthetist, dental expert, surgeon, etc., i.e. the party or subsidiary party dealing with the diagnosis and actual installation work on the respective patient. A second party B is represented by the dental technician or the dental laboratory, and a third party C is a supplier of basic elements and structural parts (cf. PROCERA). In the present case, the third party has access to automated production of the basic elements and structural parts in question. The equipment or units located with the first party are symbolized by 1, the equipment and units located with the second party are symbolized by 2, and the equipment and units located with the third party are symbolized by 3. At the first party A, the distribution between the various functions, for example a dentistry function, prosthetic function, dental expert function, surgical function, etc., is utilized in a manner known per se by the patient P. The party A can be considered as having access to X-ray functions at a hospital, clinic or corresponding establishment 4. In the present case, the third party C can own or have access (for example on a contract) to stereolithography equipment 5 of a type known per se. The first party A (i.e. the actual subsidiary party) first undertakes a preliminary examination of a patient P in order to assess whether he or she is in fact suitable or not for a fixed installation in a given jaw bone. In the first instance, the patients are completely or partially edentulous in the upper jaw, for which reason an examination of this jaw is most often carried out. It is possible per se to provide fixed installations in a lower jaw which is missing one or more teeth. In a case where it is decided that the patient is able to receive a fixed installation, the patient's jaw or jaw part must be read off or scanned. In addition, imaging of any loose prosthesis (tooth prosthesis) must be carried out. In the present case, the imaging function is indicated in FIG. 1 by means of arrows 6 and 7, where the first arrow represents the imaging of the jaw or jaw part, and the arrow 7 represents the imaging of any loose prosthesis. In cases where there is no loose prosthesis, a model is produced which could be considered to correspond to the loose prosthesis in question. In a case where the party A uses X-ray tomography, the patient is sent to a radiography department at a hospital 4 or the like if the first party A does not have such X-ray equipment. This contact between the patient and the radiography department is symbolized by 8 in FIG. 1. In a case where the radiography department at a hospital 4 or the like is used, the result of the X-ray examination can be digitalized and sent via a link 9 in digital form 10. Both the hospital 4 or the like and the equipment or unit 1 at the first party A are in this case provided with computer equipment 4a and 1a, respectively. The transfer can be done by telecommunication and/or computer links in a manner known per se.

In the case where a plastic model or a model made of other material is to be produced by means of stereolithography, the party A contacts or orders from the party C. A digital signal 11 is transmitted by the party A to the party C who imports or receives the signal 11 in computer equipment 3a. The transmission is made via a link 12 in the direction of the arrow 13. The digital signal 11 represents representations of the patient's jaw bone and loose prosthesis or equivalent. The signal 11 also represents a coordination of the imaged jaw bone and the imaged loose prosthesis and also fixture applications which have been made by the party A in a manner known per se. The link 12 can be made via telecommunication and/or computer links, which can include the Internet. Here, the expression telecommunication and/or computer links can be taken to mean the generally available links or special links. The party C contacts a fourth party (not shown in FIG. 1) if the third party C does not itself have the stereolithography equipment in question. The fourth party in this case owns the equipment in question, and the third party transfers information 12 concerning the order and information which corresponds to the readings taken by the first party A. The information 14 is digitalized and transmitted via telecommunication and/or computer links in accordance with the above. The direction of the signal is indicated in FIG. 1 by the arrow 15. The fourth party designs or produces the stereolithographic wax model and sends the latter back to the third party see the arrow 16. Debiting functions and ordering functions take place via said link 17, and the debiting functions known per se are in this case used at or by the party C. The computer equipment located with the fourth party is indicated by 5a. Information regarding the plastic model produced is sent back if appropriate to the first party A in the direction of the arrow 18. The stereolithographic actual model is transferred from the party C to the party B, see arrow 19. The second party receives, from the first party, orders to the effect that the model in question is to be produced. This ordering can be done via the telecommunication and/or computer network and has been symbolized in FIG. 1 by the digital signal 20. In addition, information 21 concerning planned treatment, individual characteristics, date, cost, etc. is transmitted to the second party B which has access to computer equipment 2a. The first party A also orders from the third party C basic arrays for the given patient type and possible auxiliary arrays which are intended to meet special characteristics of the patient. Said arrays comprise different types of basic elements, for example drills/fixtures, drill guides, guide drills and other types of drills, recessing members, fixtures, mounting spacers, screw tighteners, supports, support pins, devices, toothbrushes, cement sets, millers and machines for bite grinding and means for blocking holes, etc. The ordering and debiting functions are effected in the third party's known ordering and debiting equipment. The ordering function is digitalized and is represented by 22 in FIG. 1. The distribution path can also be considered as part of the link 12 in the direction of the arrow 18. Corresponding ordering, distribution and debiting channels are established between the second party B and the third party C. The ordering from the second party is digitalized, in the same way as above, and takes place with digital signals 23 in the direction of the arrow 24. Supplies and debiting functions from the party C to the party B take place via the link 25 in the direction of the arrow 19 by means of digital information 26 and a hardware distribution channel which can be considered as forming part of, or is symbolized by, the link 25.

The second party produces, as final products, first components which are supplied to the first party via distribution channel 27, indicated symbolically in FIG. 1, in the direction of the arrow 28. Said first components comprise an assembly template 29 which the first party uses as a hole-forming member. Also included is a unit forming the installation, for example a dental crown 30. The third party supplies second components 31 in accordance with the description given above and below.

The first party uses the assembly template for forming holes in the patient's jaw and applies the fixtures which have been obtained from the third party and are included in said second components 31. In addition, the third party supplies, inter alia, the abovementioned securing screws to the first party. The first party can form holes, apply the fixtures and anchor the installation or the dental crown to them in the abovementioned very short time. In subsidiary equipment 32 located with the first party B, use is made, inter alia, of an articulator of a type known per se. A model, for example a plaster model 33, of the opposite jaw is applied in the articulator, together with the actual model produced by stereolithography, fixture dummies and said bite register index. In this connection, soft plastic or the like is used to produce a model of the gum which will lie between the jaw-bone model and the loose prosthesis model, which is also produced by the first party. The second party produces the dental bridge with the aid of the stereolithographic plastic model, to which spacers are mounted on fixtures of the model and cementing sleeves are secured on the spacer. The frame of the dental bridge is preferably made of carbon fiber-reinforced plastic, but can also be made of titanium or a dental alloy. The soft-tissue replacement can be made of vinyl or polysiloxane. The lengths of the spacers and the configuration of the bridge with respect to soft tissues are determined and imaged. Prosthetic teeth are applied on the structural part or bridge skeleton thus formed. The tooth replacement or prosthetic teeth are worked for example from a wax model in which the prosthetic teeth are made of acrylate and have been tested on the patient. The soft tissue can be provided with small pin-shaped or spike-shaped elements which are automatically imaged in a computer program during the stereolithographic production. Said assembly template can comprise spacers which bear hole-forming sleeves or drill sleeves and are held together with the aid of said carbon fiber-reinforced plastic.

In FIG. 2, a number of patients are indicated by P, P', P", P'". These patients are assumed to turn to party A who carries out the abovementioned examination and modeling. The patients are handled by means of first equipment 34 and the first party, in accordance with the above, orders the basic sets 35, 36 and 37 and any relevant auxiliary sets 38, 39 and 40 in order to meet the type of dental treatment with its associated variations. The connections of the patients to the first party are indicated by 41, 42, 43 and 44. The distribution channels from the third unit or party C to the first unit or party A are indicated by 45, 46, 47, 48, 49 and 50. Other components, for example structural parts, tools, instruments, can also be ordered by party A from party C and are symbolized by component content 51 and the distribution path 52. Thus, for example, the wax model or a representation of the wax model can be distributed on this path. The party B can also place orders with the party C. Such orders can include models, tools, instruments, etc., and are symbolized by the component content 53 and the distribution paths 54 and 55, which for example can be parcel delivery routes. In FIG. 2, debiting functions or debiting equipment are indicated by 56 at the third party, by 57 at the second party and by 58 at the first party. Said debiting channels are established using coupled-up or fixed telecommunication and/or computer links, which also serve as the abovementioned ordering and data signal transfer channels. Thus, the party A can order equipment or a model from party C via the link 59, which is recorded by the party C and debited via the same or corresponding link. The ordering direction is indicated by 60 and the debiting direction and confirmation direction is indicated by 61. The party B can also place orders with the party C, and this is done via a link 62 in a direction indicated by 63. Debiting of the equipment or service in question can take place via a corresponding link 62 in the direction 64. In a corresponding way, ordering and debiting functions are exchanged between the units A and B via a link 65. A parcel link or hardware link 66 is also arranged between these units A and B in order to permit transfer of models from party A to party B and finished installations, templates, etc., from party B to party A. In FIG. 2, links 67 for the debiting of the patient by the party A are also indicated symbolically. In the embodiment according to FIG. 3, a large number of patients P are served by a relatively large number of first parties (dentists, prosthetists, etc.). The first parties are served in turn by a number of dental technicians or laboratories which are assumed to be present in a smaller number than the number of first parties. A third unit C (PROCERA) can serve the whole number of patients and first and second units. In accordance with the above, the third unit supplies said basic arrays 68*a*, 68*b*, 68*c* and auxiliary sets 68*a*', 68*b*' and 68*c*' belonging to these. Components, instruments, etc., are symbolized by 69 and, in accordance with the above, can be supplied to the second party B, see indicated arrows. The third party can also offer a service, which has been indicated by 70, which service can be oriented toward the patients and said first and second parties. In FIG. 3, the principal debiting function is indicated by 71. In FIG. 3, the ordering functions received in the different areas are also shown by 72, 73 and 74. The arrows shown in FIG. 3 indicate the directions of the services, components and debiting in the system.

In FIG. 4, in a block circuit diagram, the computer equipment located with the parties A, B and C is indicated by 75, 76 and 77, respectively. The computer equipment for the X-ray function and for the stereolithography function is indicated by 78 and 79. The computer equipment is connected by modem, see for example 75*a* and 76*a* on computer equipment 75 and 76, to different networks. The electronic networks or the links can consist of the general communications network which in FIG. 4 is symbolized by 80, one or more specially arranged, for example fixed, links 81 and/or computer network links 82 which can consist of or include the Internet. The computer equipment can be connected by the respective modems to one or more of said networks.

For his work, the party B (the dental technician or the dental laboratory) requires a model which images the jaw bone and the dental prosthesis with an intermediate space between these, which intermediate space actually corresponds to the space for soft tissue (gum). This permits insertion of the plastic model in an articulator (cf. above) for the opposite jaw or in a re-mounting block. In the virtual model in the computer, the positions for the fixture installations are planned in advance. Around the holes, or for forming the holes, sleeves made of solid material are needed to secure the installation of the fixture in the plastic model. That part of the plastic model which images the jaw bone is seen in FIGS. 5 and 6, where the jaw bone model has been indicated by 83 in FIG. 5. In FIG. 6, a soft-tissue imitation made of soft plastic is indicated by 84. In accordance with the above, the plastic model is obtained from the third party. A model or tooth replacement made of wax with prosthetic teeth made of acrylate is tested out in the patient's mouth and checked for the appropriate color, shape and articulation. This too is sent to the dental technician who produces the jaw-bone bridge in order to allow the acrylate teeth of the bridge to be transferred to the finished dental bridge. In addition, the party B receives a plaster model or an impression of the opposite jaw made of impression material which is not disturbed during transport to the dental technician. The bite register index can expediently be made of wax in order to permit registering of the jaws' bite relationship to each other. The insertion of the jaw models in the articulator by the dental laboratory or by the dental. technician must correspond to the bite relationships in the patient's mouth. Conventional prosthesis wax is advantageous in the present case. In addition, the second party will obtain a description of the order, the planned therapy, special requirements, for example individual characteristics and other details which concern the work, and the date when the work will be done at the clinic (at the party A).

The first party will in accordance with the above be provided with prosthetic and surgical instruments in accordance with the above. A plastic model and dental bridge will be available, likewise the abovementioned basic sets and optional auxiliary sets. The plastic model is according to the above a model of the patient's jaw which has been imaged with the aid of computerized X-ray tomography. In order to permit bite registering and mounting in the articulator, it also includes the tooth replacement. With the aid of the computer, the positions of the seats for the fixtures are determined in advance in accordance with the above, and the plastic model is then produced with the aid of stereolithography using an epoxy material in the present illustrative embodiment. The model images the jaw bone 83 and the dental prosthesis 85 (see FIG. 6) with said intermediate spaces 86 for soft tissue. The dental prosthesis model is supported on the jaw-bone model 83 with the aid of pins (not shown) which are automatically imaged in the program upon production in the stereolithography process. Suitable fixtures 87 are placed in the planned holes/seats on the model. An assembly template 88 (see FIG. 5) is produced with the aid of the model. The assembly template represents a template for drill/fixture RP. In the production of the model, the holes are strengthened with sleeves 89, and the arrangement is also such that an expansion spacer 90 and an expansion screw 91 are included in order to hold the template in a defined ideal position, even during the actual tightening when the template is not allowed to tilt in its attachments. The spacer 90 bears against the fixture 87. By means of the template production process, said template can then be transferred to the patient and there functions as a hole-forming template which provides a high degree of precision. During production of the template, the latter is provided with support parts 88a which bear against the top surface 83a of the jaw model 83. The extent of the template in or along the entire extension of the jaw bone, with its irregularities, means that the template acquires a precise position in the patient's mouth. In a preferred embodiment, the template comprises carbon fiber-reinforced plastic.

In accordance with FIG. 3, a dental bridge is produced from the plastic model part according to FIG. 6. Special spacers 92 which are intended to be used by the dental laboratory or by the dental technician are mounted on the fixtures 87 of the model and cementing sleeves 93 are applied on the spacers. The bridge skeleton 85 can consist of carbon fiber-reinforced plastic, titanium or some other dental alloy. The spacers are preferably made of titanium and in one embodiment have lengths of 3.5 and 5 mm. The spacers are intended to be cemented on the titanium sleeves 93 in the bridge in the patient's mouth and screwed tight to the fixtures using gold spacer screws 94. Tooth dummies 95 are applied on the bridge skeleton in a manner known per se.

The surgeon or equivalent exposes the maxilla at the mucolabial fold (and not at the top of the maxilla as in this case it becomes impossible to sew flaps together when the dental bridge is put in place). When the maxilla is exposed, an assembly template is applied (in a manner known per se) for drill/fixture on the dental crest with the aid of the support built on both sides of the assembly template for drill/fixture. The correct position must be found in the individual geography of the dental crest. When the assembly template for drill/fixture RP is sitting in a stable position, the work on installing fixtures can be started. The assembly template for drill/fixture is held in place in the correct position on the dental crest. A drill guide is placed in the actual sleeve on the assembly template. It is advantageous to choose a sleeve which is placed at the center over one half of the dental arch. Another sleeve is then chosen which is situated at the center of the other half of the arch. The hole-forming work can then be started. When the holes have been formed, the actual fixture is applied until contact is reached between the recessed part in the bone and the fixture. Thereafter, the assembly template is anchored in the applied fixture with the aid of the expansion spacer, after which the work on applying the fixture on the other side can proceed. When this fixture too is anchored, the assembly template is also secured to this fixture, and when the assembly template has been screwed on the first two fixtures installed, it is then possible to continue with installing the remaining fixtures, with the difference that the assembly template sits more securely in place. When all the fixtures are installed, the assembly template is unscrewed, after which the dental bridge can be applied on the fixtures which have thus been applied. The dental bridge is tested and, if necessary, adjusted with slight corrections. If, for example, one of the sleeves in the bridge does not sit exactly on the fixture, it can be adjusted for example with a round drill. Thereafter, the dental bridge is cemented, which can be done with acrylate-based cement. After the cement has hardened, the bridge can be loosened and temporarily removed. When the flap is sewn back with the fixtures underneath, the bridge is again applied on the fixtures through the soft tissue. Any bite grinding on the opposite jaw can be done, and the screw holes are filled again in the usual way.

According to the above, the dental bridge is produced on the plastic model which has been provided with fixture dummies (cf. FIGS. 5 and 6). The gum in the intermediate space between the plastic model and the tooth prosthesis model is produced in advance. Suitable holes are punched in the gum replacement over the fixtures, in which spacers of suitable length are mounted. The sleeves 93 are conical in this illustrative embodiment. The bridge skeleton 85 is made of carbon fiber-reinforced plastic, cf. said Swedish Patent 457,691. Hole perforation and sleeve application in the carbon-fiber bridge are described in more detail in the Swedish patent applications which were mentioned at the outset and which were filed on the same day as the present application. The finished carbon-fiber bridge with inserted sleeves 93 is provided in the next step with plastic teeth which are secured with fast-acting adhesive, for example cyanoacrylate, in the respective place in the silicone casting which is mounted on the patient model with the aid of rubber bands. Thereafter, a liquid composition (acryl) is applied between the plastic teeth and around the carbon-fiber skeleton in accordance with the known routine. This is polymerized in an acryl polymerization apparatus in water under pressure at a certain temperature depending on the selected process. After polymerization and cooling in cold water, the bridge is loosened and cleaned and bite-ground in the articulator according to the known routine.

FIG. 7 shows a jaw (upper jaw) indicated by 96. X-ray equipment is indicated by 97. A digital signal 98 or first representation is transmitted on a line or link 99 to the computer equipment located with the party A. FIG. 7 also shows a loose prosthesis or a model of a tooth replacement indicated by 100. This too is read off, for example by computer tomography, laser scanning, photogrammetry, etc., which transmits to said computer equipment a digital signal 103 or second representation on a link 104. A user 105 operates the computer terminal 106 in order, by means of a computer program 107 of a known type, to simulate virtual images 108 and 109 on the computer screen 110 of said representations 98 and 103, i.e. of the jaw bone and the loose prosthesis or model thereof, respectively. The user coordinates the virtual images and plans optimal applications of virtual fixtures 111, 112 in the actual jaw bone. The coordinated configuration of jaw bone, prosthesis and fixtures is exported digitally to the party C in accordance with the above. The signal has in this case been indicated by 113, while the link has been indicated by 114. The party C deals, in accordance with the above, with the production of a plastic model which includes the jaw bone, the prosthesis (or equivalent) and replacements (tube elements) for the fixtures or the fixture positions. The model is sent as a parcel which has been symbolized by the link 115.

According to the above, the party A also provides the party B with a model or impression 116 of the patient's lower jaw which has been symbolized by 117. According to the above, the party B produces an assembly template 118 for the party A, which template is used for guiding hole-forming members (drill) 119. Preliminary drilling 120 has in this case been carried out with a small drill. FIG. 7 also shows that a fixture 121 has been installed in the jaw bone 96. An articulator 122 is shown symbolically by 122, in which the plastic model 123 which was obtained from the party C has been placed together with the impression 116' which was received from the party A. The abovementioned space 124 for the soft tissue or gum is simulated in the articulator. The transfer link for the impression (of plaster) has been shown by 125.

In accordance with the invention and FIGS. 8 and 9, a file system is used for handling customers, orders, production, etc. This file-handling is intended to be done in a computer arrangement, but in order to clearly illustrate the functions outside the computer world, these have been indicated by symbolic hardware. The system is made up of modules, where one module 126 has been. indicated with a file holder 127 which can be withdrawn from and inserted into a filing cabinet 128. The file holder contains a number of files or sections, where a first file has been indicated as an order file 129, a second file as a finance file 130, a third file as an invoice file 131, a fourth file as a product or component file 132, and a fifth file as a customer file 133. The content of the file holder 127 can relate to a certain number of customers, and the module system as a whole is designed so that incoming customers can be received by expanding the number of file holders or modules 127. The different file holders have substantially identical or corresponding contents, and in FIG. 8 an inserted file holder has been indicated by 134.

In FIG. 9, the structure of the module system has been indicated by three cabinets 126', 126" and 126'''. The first cabinet 126' contains file holders 127', 134' etc. in accordance with the above. The cabinets 126" and 126''' have substantially the same or corresponding structure. The contents of the different cabinets can be coordinated, which has been symbolized by the link 135, which is also indicated symbolically. In accordance with FIG. 9, the flow of incoming orders and the production of products can be separated. In FIG. 9, an order station, which can be the producer itself or the customer directly, is indicated by 136. In the present case, an order document is shown (i.e. an order file) by 137. The document is transferred in the direction of the arrow 138 to the storage system which is indicated by 139 and which is arranged between the order sender and the production function. The transfer 138 takes place digitally, in accordance with the above, via an electronic link or wireless communication in a manner known per se. The production function is indicated by 140, and the production function can extract or import a document (or a file) 16 to or from. the storage function 139. The transfer direction for the document 141 is indicated by 142. This connection too can be wired or wireless in accordance with the above.

In accordance with the invention, as is shown in FIG. 10, a flow chart can be set up for treating an edentulous patient with a dental plate. The patient is defined with respect to certain parameters, for example jaw-bone status, age, etc. This definition takes place in the block 143. Thereafter, the patient's status is defined in relation to earlier experience in the block 144. This comparison function can be performed by the surgeon or prosthetist. Advantages of the desired dental situation are defined in the block 145. This definition takes place on consultation between patient and surgeon.. A model production, for example production of a drill model, is defined in block 146. The X-ray situation is defined in the block 147, for example whether X-ray tomography will be used, whether this will be done at hospital or by computer tomography. The production function using preferably three-dimensional CADD equipment is defined in block 148. If stereolithography equipment is to be used for producing the model, this is done in block 149. A plastic model with fixture markings is defined in a block 150. Thereafter, the dental technician's work is defined in block 151. Preparations for surgery are defined in block 152. The other parameters used for data programming are implemented, see above.

The invention is not limited to the embodiment described above by way of example, and instead it can be modified within the scope of the attached patent claims and the inventive concept.

The invention claimed is:

1. A method for allocating prosthetic installation work between at least three parties where a dental situation and fixture applications therein are simulated on a computer screen by the first party, first components in connection with the prosthetic installation are produced by the second party with the aid of a recording and said simulation, second components are supplied by the third party, and the prosthetic installation is assembled and fitted by the first party by means of said first and second components, characterized in that the recording includes a first reading of an impression or prosthesis and a second reading of a portion supporting the prosthetic installation, in that the simulation includes collation of images or representations on the computer screen, which images or representations result from the first and second readings and on the basis of which the simulated fixture applications are constructed, in that the simulated fixture applications include chosen positionings in relation to said supporting portion, in that a model, e.g. of plastic, is produced, preferably by a stereolithopaphy method, by one of said parties, or a fourth party, in that the first components include an assembly template which can be applied to said substrate and is produced by means of the model and is intended for hole-forming members which are guided by the assembly template in the substrate in directions which correspond to the directions of the chosen positionings, in that the first components include a unit forming part of the installation, e.g. a dental bridge, which is provided with attachment holes which connect to the holes formed in the substrate, in that the second components include the fixtures which are applied in said formed holes by the first party, and in that the second components also include securing members for securing the unit in said applied fixtures.

2. The method as claimed in patent claim 1, characterized in that the model is constructed, preferably by the third party, in two parts, where the first part represents the supporting portion (jaw bone) and the second part represents the tooth prosthesis/tooth structure, the two parts being separated from each other by an intermediate space to permit application in an articulator.

3. The method as claimed in patent claim 1, characterized in that the first party sends order descriptions by means of completely or partially automated equipment to the second party who receives the order via completely or partially automated receiving equipment.

4. The method as claimed in claim 1, characterized in that the dental bridge is produced on the plastic model, and in that spacers are mounted on the fixtures of the model and cementing sleeves are placed on the spacers, and in that the frame of the dental bridge is preferably made of carbon fiber-reinforced plastic, titanium or a dental alloy.

5. The method as claimed in claim 1, characterized in that a soft-tissue replacement is between the first and second parts and is made of soft plastic, e.g. vinyl or polysiloxane, and in that the lengths of the spacers are secured to, and the configuration of the bridge is adapted to, the soft-tissue.

6. An arrangement for allocating prosthetic installation work between at least three parties, and comprising a computer which is located with the first party and which is intended to simulate, on its screen, a dental situation and fixture applications therein, a first production unit which is located with the second party and which is intended to permit production of first components intended for the prosthetic installation with the aid of a recording and said simulation, a second production or supply unit which is located with the third party and which is used to produce second components, and first equipment which is located with the first party and is intended to allow the prosthetic installation to be constructed and fitted on the patient with the aid of the first and second components, characterized in that the recording includes a first reading of an impression or prosthesis and a second reading of a portion supporting the prosthetic installation, in that the computer is intended, in connection with the simulation, to permit collation of images or representations on the computer screen, which images or representations result from the first and second readings, and to indicate on these the simulated fixture applications which include chosen positionings in relation to said supporting portion, in that second equipment, preferably a stereolithography appliance, which is located with one of the parties, or with a fourth party, is intended for production of a model, e.g. of plastic, in that the first production apparatus is provided for production of an assembly template which has been constructed by means of the model and which has guide elements for hole-forming members which can be guided by the assembly template in order to assume directions which correspond to the directions of the chosen positionings, in that the first production apparatus is also provided for production of a structural unit, e.g. a dental bridge, which forms part of the installation and which is provided with attachment holes which connect to the holes formed in the substrate, in that the second production or supply unit produces or supplies the fixtures intended for said formed holes, and also securing members for securing the structural unit in the fixtures which are applied in the substrate.

7. The arrangement ms claimed in patent claim 6, characterized in that the model, e.g. the plastic model, consists of two parts, where the first part simulates the supporting portion and the second part simulates the impression/prosthesis/tooth structure, and in that between the parts there is an intermediate space which corresponds to the site for soft tissue, which intermediate space permits fitting/impaction in an articulator of an opposite jaw.

8. The arrangement as claimed in patent claim 6, characterized in that the tooth structure comprises wax with prosthetic teeth made of acrylate and is tested on the patient.

9. The arrangement as claimed in claim 6, characterized in that the first party uses completely or partially automated ordering equipment, which for example includes an order telephone, telecommunications network or computer network, to send an order to the second party concerning the planned therapy, individual characteristics, date, cost, etc., and in that the second party has access to completely or partially automated receiving equipment.

10. The arrangement as claimed in claim 6, characterized in that the recording includes information on the relationship of the jaw bites to each other, and in that the information to the second party includes details of the articulator/articulators, the information preferably being able to be transmitted to the second party by electronic means.

11. The arrangement as claimed in claim 6, characterized in that the model which can be produced by the first party, for example by means of X-ray tomography, can be transmitted to the second party or the third party by completely or partially electronic means, e.g. via computer and/or telecommunication systems (including the Internet), and in that the third party, e.g. with the aid of the first production unit, constructs a real (actual) model which is sent to the first party or the second party.

12. The arrangement as claimed in patent claim 11, characterized in that the first part is supported on the second part with the aid of small pin-shaped or spike-shaped elements which are automatically simulated in a computer program for stereolithography production.

13. The arrangement as claimed in patent claim 11, characterized in that the model is provided with fixtures placed in holes or seats in the model, and in that the assembly template is adapted to said fixtures/holes/seats.

14. The arrangement as claimed in claim 6, characterized in that the assembly template comprises spacers which support hole-forming sleeves or drill sleeves, in that the spacers are held together with the aid of carbon fiber-reinforced plastic, and in that the template is assigned a contact with the second model part which corresponds to the patient's jaw bone, the template being able to be placed in a corresponding position in the patient's mouth.

15. The arrangement as claimed in claim 6, characterized in that the dental bridge comprises spacers which can be mounted on the fixtures of the model, and in that cementing sleeves are arranged on the spacers, and the frame (skeleton) of the dental bridge consists of carbon fiber-reinforced plastic, titanium or some other dental alloy.

16. The arrangement as claimed in claim 6, characterized in that a soft tissue replacement is in said intermediate spaces and is made of soft plastic.

17. The arrangement as claimed in claim 6, characterized in that the spacers comprise titanium and are intended to be cemented on the titanium sleeves in the bridge in the patient's mouth and to be screwed to the fixtures with spacer screws made of gold.

18. The arrangement as claimed in claim 6, characterized in that the second components comprise assembly templates for drills/fixtures RP, drill guides, guide drills and other types of drills, recessing members, fixtures, assembly spacers, screw tighteners, supports, guide pins, mandrels, toothbrushes, cement compositions, milling devices and machines for bite grinding and hole-blocking means, which second components are arranged in different platforms with different dimensions.

19. The arrangement as claimed in claim 6, characterized in that the first apparatus is designed to permit, upon transfer of the first and second components, a short time for fitting the installation on the patient of 1 to 4 hours, preferably 1½ to 2 hours.

* * * * *